United States Patent
Zhou et al.

(10) Patent No.: US 11,635,426 B2
(45) Date of Patent: Apr. 25, 2023

(54) TEST STRIP AND KIT FOR TESTING MYCOPHENOLIC ACID AND PREPARATION METHOD OF TEST STRIP

(71) Applicant: BEIJING DIAGREAT BIOTECHNOLOGIES CO., LTD., Beijing (CN)

(72) Inventors: Jianping Zhou, Beijing (CN); Yujun Zhou, Beijing (CN); Xiuli Xu, Beijing (CN)

(73) Assignee: BEIJING DIAGREAT BIOTECHNOLOGIES CO., LTD., Beijing (CN)

( * ) Notice: Subject to any disclaimer, the term of this patent is extended or adjusted under 35 U.S.C. 154(b) by 871 days.

(21) Appl. No.: 16/557,005

(22) Filed: Aug. 30, 2019

(65) Prior Publication Data
US 2021/0025880 A1   Jan. 28, 2021

(30) Foreign Application Priority Data

Jul. 26, 2019 (CN) .......................... 201910682034.6

(51) Int. Cl.
*G01N 33/543* (2006.01)
*G01N 33/94* (2006.01)

(52) U.S. Cl.
CPC ... *G01N 33/54366* (2013.01); *G01N 33/9493* (2013.01); *G01N 2430/00* (2013.01)

(58) Field of Classification Search
CPC ......... G01N 2430/00; G01N 33/54366; G01N 33/558; G01N 33/9493
See application file for complete search history.

(56) References Cited

U.S. PATENT DOCUMENTS 6,159,698 A      12/2000  Staples et al.
6,225,073 B1 *   5/2001   Alexander ........... C07D 307/88
                                                         530/404

FOREIGN PATENT DOCUMENTS

| CN | 101762692 A | * | 6/2010 |
| CN | 104597238 A |   | 5/2015 |
| CN | 107976541 A |   | 5/2018 |
| CN | 109061144 A | * | 12/2018 |

OTHER PUBLICATIONS

CN 109061144 A, published Dec. 21, 2018, machine translation.*
CN 101762692 A, published Jun. 30, 2010, machine translation.*
CN 107102144 A, published Aug. 29, 2017, English Abstract.*

* cited by examiner

*Primary Examiner* — Galina M. Yakovleva
(74) *Attorney, Agent, or Firm* — Buchanan, Ingersoll & Rooney PC

(57) ABSTRACT

A test strip and kit for testing mycophenolic acid and a preparation method of the test strip are described. The test strip includes a bottom plate and a sample pad, a glassfiber membrane, a nitrocellulose membrane and an absorbent paper which are successively lapped on a surface of the bottom plate, the sample pad is treated by a sample pad treatment fluid; the glassfiber membrane is treated by a glassfiber membrane treatment fluid; the glassfiber membrane is coated by a mycophenolic acid specific-antibody conjugate; the nitrocellulose membrane is provided with a detection line and a quality control line; and a mycophenolic acid protein conjugate is sprayed on the detection line.

16 Claims, 1 Drawing Sheet

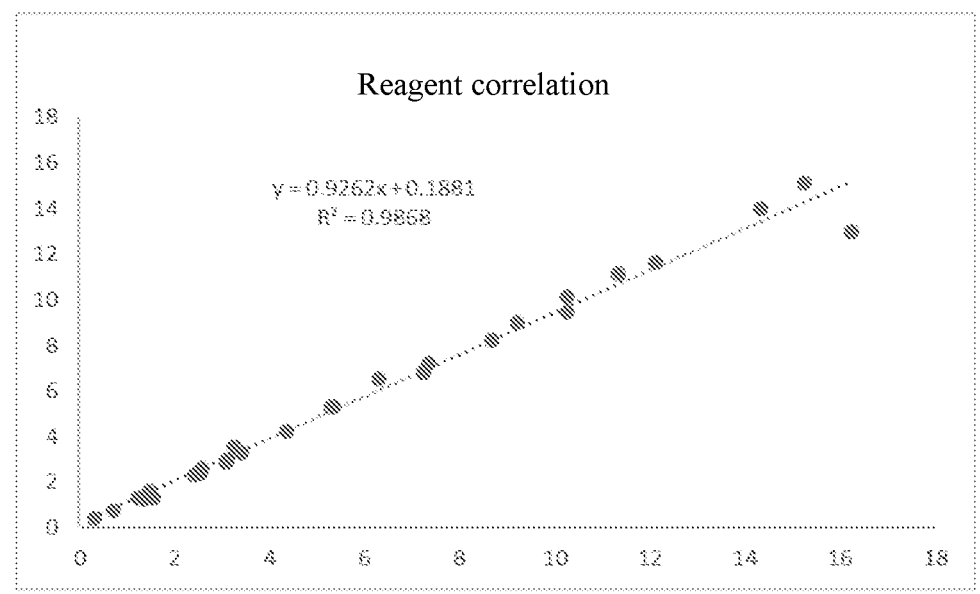

US 11,635,426 B2

TEST STRIP AND KIT FOR TESTING MYCOPHENOLIC ACID AND PREPARATION METHOD OF TEST STRIP

TECHNICAL FIELD

The present invention belongs to the technical field of mycophenolic acid testing, and specifically relates to a test strip and kit for testing mycophenolic acid (MPA) and a preparation method of the test strip.

TECHNICAL BACKGROUND

MPA, also called mycophenolic acid, can noncompetitively bond with inosine monophosphate dehydrogenase, and the latter one is a key enzyme to the denovo synthesis of guanine nucleotides of TB lymphocyte in its proliferation process. As immunosuppressors, the mycophenolate mofetil derivatives have been widely used in the prevention and treatment of acute rejection of the transplanted organs at home and abroad. Mycophenolate mofetil is transformed to mycophenolic acid in vivo to exert its immunosuppression activity. In different transplanted groups, great disparities of mycophenolic acid pharmacokinetics can be found among individuals, and moreover, its pharmacokinetics will be influenced by in vivo/vitro factors.

With the proposal of precision medicine and individualized medicine, various kinds of drug concentration testing get more and more attention. Excessive metabolic concentration of mycophenolic acid in blood will inhibit immunological competence excessively, resulting in hypoimmunity and other problems; too low metabolic concentration of mycophenolic acid in blood will not bring due immunosuppression, resulting in the failure of a therapeutic action to acute rejection of the transplanted organs. Therefore, the significance of mycophenolic acid testing becomes particularly outstanding.

At present, the common testing methods for mycophenolic acid mainly include mass-spectrography, high performance liquid chromatography, chemiluminescent immunoassay, homogeneous enzyme immunoassay, etc. Mass-spectrography refers to a method that moving ions are separated by electric field and magnetic field for testing according to the mass-to-charge ratio, and the testing is conducted by a mass spectrometer. High performance liquid chromatography refers to a method that with liquid as mobile phase, a high-pressure transfusion system is taken to pump a single solvent with different polarities or a mixed solvent different proportions, a buffer solution and other mobile phase into a chromatographic column loaded with stationary phase, each component is put into a detector after being separated in the column, thus achieving sample analysis, and the analytical instrument is high performance liquid chromatograph. Chromatography and mass-spectrography have precise testing results, but the sample needs to be pretreated before loading, taking too much detection time, and only one sample can be loaded every time, incapable of satisfying high throughput requirement, and the testing instrument used is relatively expensive, restricting its clinical popularization to some extent. Turbidimetry is mainly applied by Roche for testing, the method needs to be equipped with a high-cost biochemical analyzer and the reagent needs to be refrigerated, which is incapable of satisfying the increasing clinical testing requirement and achieving single testing in any time. Mycophenolic acid was tested by homogeneous enzyme immunoassay (EVERMED, application No.: 201510039618.3). By an immune method, multiple samples can be measured on an automatic biochemical analyzer at the same time to achieve high-throughput and rapid measurement. The method requires an automatic biochemical analyzer, 2-8° C. storage temperature and cold-chain transportation, therefore, the method fails to achieve a single package and timely monitoring in medication departments.

SUMMARY

In view of this, an objective of the present invention is to provide a test strip and kit for testing mycophenolic acid and a preparation method of the test strip; the test strip can effectively make up the gaps of the several methods above and can achieve normal temperature preservation, rapid, high throughput and single testing in any time, thus greatly improving the test cost, operation convenience and clinical use simplicity of the test strip.

To achieve the above objective of the invention, the present invention provides the following solution.

A test strip for testing the content of mycophenolic acid includes a bottom plate and a sample pad, a glassfiber membrane, a nitrocellulose membrane and an absorbent paper which are successively lapped on a surface of the bottom plate, where the sample pad is treated by a sample pad treatment fluid, and the sample pad treatment fluid includes a buffer solution, an active protein and a surfactant;

the glassfiber membrane is treated by a glassfiber membrane treatment fluid, and the glassfiber membrane is coated by a mycophenolic acid specific-antibody conjugate; and the mass concentration of the mycophenolic acid specific-antibody conjugate is 0.1-0.3%, and the coating concentration of the mycophenolic acid specific-antibody conjugate is 0.5-1 mg/mL;

the nitrocellulose membrane is provided with a detection line and quality control line, a mycophenolic acid protein conjugate is sprayed on the detection line, the concentration of the mycophenolic acid protein conjugate is 1-3 mg/ml, and the spraying amount is 1-3 μL/cm.

Preferably, the buffer solution in the sample pad treatment fluid is selected from one or more of PBS buffer solution, TRIS buffer solution and glycine buffer solution; the active protein in the sample pad treatment fluid is selected from one or more of bovine serum albumin, casein and ovalbumin; the surfactant in the sample pad treatment fluid is selected from one or more of Tween® 20 (polyoxyethylenesorbitan monolaurate) and Tween® 80 (polyoxyethylenesorbitan monooleate).

Preferably, the conjugate in the mycophenolic acid specific-antibody conjugate is a colloidal gold particle or a fluorescent microsphere.

Preferably, the glassfiber membrane treatment fluid includes a basal solution and the following components at concentrations below: 0.5-5 g/L polyethylene glycol 6000, 3-15 g/L mannitol, 0.1-1.5 g/L alum and 0.8%-1.0% sodium chloride; the basal solution is selected from one or more of PBS buffer solution, TRIS buffer solution and glycine buffer solution.

A preparation method of the above test strip includes the following steps of:

1) treating the sample pad by the sample pad treatment fluid to obtain a treated sample pad;

2) mixing mycophenolic acid monoclonal antibodies and the conjugate for coupling and sealing to obtain a mycophenolic acid specific-antibody conjugate; spraying the mycophenolic acid specific-antibody conjugate on the treated glassfiber membrane to obtain the glassfiber membrane coated by the mycophenolic acid specific-antibody conjugate;

3) spraying the mycophenolic acid protein conjugate on the detection line of the nitrocellulose membrane and spraying goat-anti-mouse IgG on the quality control line to obtain a nitrocellulose membrane sprayed with the detection line and quality control line;

4) successively lapping and pasting the treated sample pad, the glassfiber membrane coated by the mycophenolic acid specific-antibody conjugate, the nitrocellulose membrane provided with the detection line and quality control line as well as the absorbent paper on the surface of the bottom plate to obtain the test strip;

where, there is no limitation on an execution sequence of steps 1), 2) and 3).

Preferably, the concentration of mycophenolic acid monoclonal antibodies of the coupling system in step 2) is 100-500 μg/mL; and the coupling time is 2.5-3.5 h.

Preferably, the mycophenolic acid protein conjugate is sprayed after mixed with a spraying buffer solution; components of the spraying buffer solution are the same as those of the glassfiber membrane treatment fluid.

A kit including the above test strip is provided, where the kit further includes a mycophenolic acid QC substance.

Preferably, the mycophenolic acid QC substance is obtained by mixing and lyophilizing pure mycophenolic acid and a lyophilized buffer solution.

Preferably, the lyophilized buffer solution includes a basal solution and the following components at concentrations below: 2-6 g/L polyethylene glycol, 3-8 g/L trehalose, 5-20 g/L mannitol, 1 wt % polyvinylpyrrolidone; the basal solution is selected from one or more of TRIS buffer solution, phosphoric acid buffer solution, boric acid buffer solution and phosphate buffer solution; pH of the basal solution is 7.6-8.6; the solute concentration of the basal solution is 50-200 mmol/L.

Beneficial effect of the present invention: the test strip provided by the present invention can rapidly test the content of mycophenolic acid in blood samples, and the testing instrument has low cost, simple and rapid operation; the test strip has good stability and can be stored at room temperature for transportation with 18 months of shelf life at 2-30° C.; meanwhile test samples are extensive, including serum samples, plasma samples and whole blood samples, while the whole blood sample cannot be tested by the method of prior art; the linear range is wide, being up to 0-20 μg/mL; the test strip has a stronger anti-interference capability, after 50 mg/ml hemoglobin and 50 mg/dl triglyceride are added for interference, compared with the results obtained before adding interfering substances, the relative deviation is less than 5% within the acceptable range, therefore, the anti-interference capability is strong.

BRIEF DESCRIPTION OF THE DRAWINGS

FIG. 1 is a curve chart showing clinic correlation of reagents.

DETAILED DESCRIPTION

The present invention provides a test strip for testing the content of mycophenolic acid, including a bottom plate and a sample pad, a glassfiber membrane, a nitrocellulose membrane and an absorbent paper which are successively lapped on a surface of the bottom plate.

There is no special limitation to texture and source of the bottom plate in the present invention, and conventional texture and source of the test strip in this field are available.

In the present invention, the sample pad is treated by a sample pad treatment fluid, and the sample pad treatment fluid includes a buffer solution, an active protein and a surfactant; in the present invention, the buffer solution in the sample pad treatment fluid is selected from one or more of PBS buffer solution, TRIS buffer solution and glycine buffer solution; the active protein in the sample pad treatment fluid is selected from one or more of bovine serum albumin, casein and ovalbumin; the surfactant in the sample pad treatment fluid is selected from one or more of Tween® 20 (polyoxyethylenesorbitan monolaurate) and Tween® 80 (polyoxyethylenesorbitan monooleate). In specific implementation process of the present invention, the sample pad treatment fluid is preferably a PBS buffer solution added 0.1% Tween® 20 (polyoxyethylenesorbitan monolaurate). In the present invention, the sample pad treatment is preferably to soak the sample pad into the sample pad treatment fluid for 0.5 h and then put it into an oven for drying for 2 h at 65° C.

In the present invention, the glassfiber membrane is coated by a mycophenolic acid specific-antibody conjugate, and the mass concentration of the mycophenolic acid specific-antibody conjugate is 0.1-0.3%, and the coating concentration of the mycophenolic acid specific-antibody conjugate is preferably 0.5-1 mg/mL. In the present invention, the conjugate in the mycophenolic acid specific-antibody conjugate is preferably a colloidal gold particle or fluorescent microsphere; in the present invention, grain size of the colloidal gold particle is preferably 10-50 nm, and grain size of the fluorescent microsphere is preferably 100-200 nm; there is no special limitation to the source of the fluorescent microsphere in the present invention, and the conventional commercial fluorescent microsphere in this field is available.

In the present invention, the glassfiber membrane is treated by a glassfiber membrane treatment fluid. In the present invention, the glassfiber membrane treatment fluid includes a basal solution and the following components at concentrations below: 0.5-5 g/L polyethylene glycol 6000, 3-15 g/L mannitol, 0.1-1.5 g/L alum and 0.8%-1.0% sodium chloride; the basal solution is selected from one or more of PBS buffer solution, TRIS buffer solution and glycine buffer solution; the basal solution is preferably selected from one or more of PBS buffer solution, TRIS buffer solution and glycine buffer solution. In the present invention, when the marked conjugate is a fluorescent microsphere, preferably, TRIS buffer solution is served as the basal solution of the glassfiber membrane treatment fluid, the concentration of the TRIS buffer solution is preferably 40-60 mmol/L, more preferably 50 mmol/L; the glassfiber membrane treatment fluid more preferably includes the following components: 3 g/L polyethylene glycol, 1.2 g/L alum, 4 g/L mannitol and 0.9% sodium chloride. In the present invention, when the marked conjugate is a colloidal gold particle, boric acid buffer solution is served as the basal solution of the glassfiber membrane treatment fluid, the concentration of the boric acid buffer solution is preferably 15-25 mmol/L, more preferably 20 mmol/L; the glassfiber membrane treatment fluid more preferably includes the following components at concentrations below: 0.5 g/L polyethylene glycol, 0.2 g/L alum, 4 g/L mannitol and 0.9% sodium chloride.

In specific implementation process of the present invention, the glassfiber membrane is dried after being soaked in the glassfiber membrane treatment fluid; the soaking time is preferably 12-17 min, more preferably 15 min; the drying temperature is preferably 63-68° C. and the drying time is preferably 2 h.

In the present invention, the nitrocellulose membrane is provided with a detection line and quality control line, a mycophenolic acid protein conjugate is sprayed on the detection line, the concentration of the mycophenolic acid protein conjugate is 1-3 mg/ml, and the spraying amount is 1-3 μL/cm. In the present invention, the mycophenolic acid protein conjugate is preferably mycophenolic acid-coupled bovine serum albumin or mycophenolic acid-coupled ovalbumin; in the present invention, goat-anti-mouse IgG is sprayed on the quality control line, and the concentration of the goat-anti-mouse IgG is preferably 1-3 mg/ml, and the spraying amount is 1-3 μL/cm.

The present invention further provides a preparation method of the test strip, including the following steps of: 1) treating the sample pad by the sample pad treatment fluid to obtain a treated sample pad; 2) mixing mycophenolic acid monoclonal antibodies and the conjugate for coupling and sealing to obtain a mycophenolic acid specific-antibody conjugate; spraying the mycophenolic acid specific-antibody conjugate on the treated glassfiber membrane to obtain the glassfiber membrane coated by the mycophenolic acid specific-antibody conjugate; 3) spraying the mycophenolic acid protein conjugate on the detection line of the nitrocellulose membrane and spraying goat-anti-mouse IgG on the quality control line to obtain a nitrocellulose membrane sprayed with the detection line and quality control line; 4) successively lapping and pasting the treated sample pad, the glassfiber membrane coated by the mycophenolic acid specific-antibody conjugate, the nitrocellulose membrane provided with the detection line and quality control line as well as the absorbent paper on the surface of the bottom plate to obtain the test strip; there is no limitation on an execution sequence of steps 1), 2) and 3).

In the present invention, the sample pad is treated by the sample pad treatment fluid to obtain the treated sample pad. In the present invention, the sample pad treatment is preferably to soak the sample pad into the sample pad treatment fluid for 0.5 h and then put it into an oven for drying for 2 h at 65° C.

In the present invention, mycophenolic acid monoclonal antibodies are mixed with the conjugate for coupling and sealing to obtain the mycophenolic acid specific-antibody conjugate. In the present invention, the mycophenolic acid monoclonal antibodies are preferably purchased from Beijing Deaoping Biotech Co., Ltd. with the item number of ATDMMPA-01. In the present invention, when the conjugate is a fluorescent microsphere, the mycophenolic acid monoclonal antibodies, EDC and fluorescent microsphere solution are mixed, and in the coupling system of the present invention, the concentration of the mycophenolic acid monoclonal antibodies is preferably 100-500 μg/mL, more preferably 200-400 μg/mL; the concentration of the fluorescent microsphere is preferably 0.5%-1.5%, more preferably 1%; the concentration of the EDC is preferably 8-12 mg/mL, more preferably 10 mg/mL; in the present invention, 20 mmol/L phosphate buffer is served as a solvent of the coupling system. In the present invention, the coupling time is preferably 2.5-3.5 h, more preferably 3.0 h. In the present invention, preferably, the coupling system is centrifuged after coupling and before sealing to remove supernatant; there is no special limitation to the centrifugal speed and time in the present invention as long as solid can be separated from liquid available. In the present invention, sealing is conducted after the centrifugation. In the present invention, the sealing is preferably conducted by bovine serum albumin solution, and the sealing time is preferably 50-70 min, more preferably 60 min. In the present invention, the mass concentration of the bovine serum albumin solution is preferably 0.8%-1.2%, more preferably 1.0%.

In the present invention, when the conjugate is a colloidal gold particle, grain size of the colloidal gold particle is preferably 10-50 nm; in the present invention, the colloidal gold particle is preferably a commercial product or homemade product, when the colloidal gold particle is a homemade product, it is preferably prepared by a conventional reduction method of trisodium citrate. In the present invention, when the colloidal gold particle is served as the conjugate for coupling, preferably, the colloidal gold solution is mixed with the mycophenolic acid monoclonal antibodies well, no EDC is added and a physical absorption principle is taken; the coupling time is preferably 2.5-3.5 h, more preferably 3.0 h; In the present invention, preferably, the coupling system is centrifuged after coupling and before sealing to remove supernatant; there is no special limitation to the centrifugal speed and time in the present invention as long as solid can be separated from liquid available.

After the mycophenolic acid specific-antibody conjugate is prepared in the present invention, the mycophenolic acid specific-antibody conjugate is sprayed on the treated glassfiber membrane to obtain the glassfiber membrane coated by the mycophenolic acid specific-antibody conjugate. In the present invention, preferably, the mycophenolic acid protein conjugate is sprayed after mixed with a spraying buffer solution; components of the spraying buffer solution are preferably the same as those of the glassfiber membrane treatment fluid. In the present invention, the concentration of the mycophenolic acid specific-antibody conjugate in the spraying liquor is preferably 0.1%-0.3%, more preferably 0.2%. In the present invention, the spraying is preferably conducted by a gold dispenser system, at the end of the spraying, drying is conducted preferably, the drying temperature is preferably 45-65° C., the drying time is preferably 2-6 h, and the drying is preferably conducted in an air dry oven.

In the present invention, mycophenolic acid protein conjugate is sprayed on the detection line of the nitrocellulose membrane and goat-anti-mouse IgG is sprayed on the quality control line to obtain the nitrocellulose membrane sprayed with detection line and quality control line. In the present invention, the mycophenolic acid bovine serum albumin is preferably mycophenolic acid-coupled bovine serum albumin or mycophenolic acid-coupled ovalbumin. In the present invention, the spraying concentration of the mycophenolic acid protein conjugate is preferably 1-3 mg/mL, the spraying amount of the mycophenolic acid protein conjugate is preferably 0.5-1 mg/mL, the spraying concentration of the goat-anti-mouse IgG is preferably 1-3 mg/mL, and the spraying amount of the goat-anti-mouse IgG is 0.5-1 mg/mL. In the present invention, at the end of the spraying, drying is conducted preferably, the drying temperature is preferably 45-65° C., the drying time is preferably 2-6 h, and the drying is preferably conducted in an air dry oven.

In the present invention, after preparing the treated sample pad, the glassfiber membrane coated by the mycophenolic acid specific-antibody conjugate, the glassfiber membrane provided with the detection line and quality control line, the treated sample pad, the glassfiber membrane coated by the mycophenolic acid specific-antibody conjugate, the glassfiber membrane provided with the detection line and quality control line as well as the absorbent paper are successively lapped and pasted on the surface of the bottom plate to obtain the test strip. In the present invention, when the test strip is used to test whole blood, a blood filtering membrane is added between the sample pad and the dried nitrocellulose membrane, the blood filtering membrane is a commercial product, namely, the sample pad, the blood filtering membrane, the dried glassfiber membrane, the dried nitrocellulose membrane and the absorbent paper are successively pasted on the surface of the bottom plate to obtain the test strip.

The present invention preferably further includes a trimming step of the test strip, there is no special limitation to the trimming step in the present invention, and a conventional trimming method in this field is available. In the present invention, after preparation, the trimmed test strip is preferably put into a reagent card, drying agent is added and sealed by an aluminium foil bag to obtain a final test strip.

The present invention further provides a kit including the test strip, further including a mycophenolic acid quality control (QC) substance. In the present invention, the mycophenolic acid QC substance is preferably obtained by mixing and lyophilizing pure mycophenolic acid and a lyophilized buffer solution. In the present invention, the lyophilized buffer solution preferably includes a basal solution and the following components at concentrations below: 2-6 g/L polyethylene glycol, 3-8 g/L trehalose, 5-20 g/L mannitol, 1 wt % polyvinylpyrrolidone; the basal solution is selected from one or more of TRIS buffer solution, phosphoric acid buffer solution, boric acid buffer solution and phosphate buffer solution; pH of the basal solution is preferably 7.6-8.6; the solute concentration of the basal solution is preferably 50-200 mmol/L. In the present invention, the mycophenolic acid QC substance preferably includes several mycophenolic acid QC substances at different concentrations. The test strip is applied in the present invention to test mycophenolic acid QC substances at different concentrations to obtain a curvilinear relationship between C/T values and concentrations of mycophenolic acid, thus quantitatively testing the content of mycophenolic acid in samples.

The technical solution provided by the present invention will be described in detail with reference to embodiments hereby, but these embodiments should be not construed as limiting the scope of the invention.

EMBODIMENT 1

Preparation of a test strip:

1) The sample pad was soaked into a sample pad treatment fluid for 0.5 h and put into an oven for drying for 2 h at 65° C.;

2) Fluorescent microsphere (grain size=100 nm) was taken; 1% fluorescent microsphere, 10 mg/mL EDC and 200 µg/mL mycophenolic acid monoclonal antibodies were added to 20 mmol/L phosphate buffer solution as a solvent for mixing well and coupling for 3 h, centrifuged to remove the supernatant, then 1% BSA was added for sealing for 1 h.

3) The prepared marked conjugate was centrifuged and resuspdended by a resuspending buffer solution (50 mm TRIS buffer solution, 3 g/L polyethylene glycol, 1.2 g/L alum, 4 g/L mannitol and 0.9% sodium chloride) to concentration=0.2%, and the glassfiber membrane was soaked by a pretreating buffer solution (its components and content are consistent with the resuspending buffer solution) and dried for 1 h; a gold dispenser system was used to spray the resuspended solution on the glassfiber membrane, and then it was dried by an air dry oven for 2 h at 65° C.;

4) Line T represented mycophenolic acid-coupled BSA and the concentration was 1 mg/ml; line C represented goat-anti-mouse IgG and the concentration was 1 mg/ml; the conjugate and quality control line are respectively dispersed on line T and line C of the nitrocellulose membrane, and then it was dried by an air dry oven for 2 h at 65° C.;

5) The sample pad, blood filtering membrane, dried glassfiber membrane, dried nitrocellulose membrane and absorbent paper were successively pasted on the bottom plate; a big reagent board was trimmed and loaded into a reagent card, was added a drying agent and sealed by an aluminium foil bag to obtain the test strip;

The blood filtering membrane is used for measuring whole blood, not for the measurement of serum in normal condition, and it is a commercial product.

Preparation of a calibration curve:

Mycophenolic acid calibration products at concentrations of 0, 1.25, 2.5, 5, 10, 20 µg/mL were dropwise added to a reagent card and mixed well for standing chromatography for 15 min, where 3 reagent cards were set for each concentration, the fluorescence signal value was read by an immune fluoroanalyzer, and T/C value was calculated to establish a calibration curve, and the results were shown in FIG. 1, where X-axis is the concentration of calibration products, Y-axis is T/C value. It can be seen from FIG. 1 that samples at different concentrations are tested within the whole linear range, testing results CVs are less than 10%, indicating good repeatability and satisfying test requirements.

Test of sample repeatability:

Test samples were dropwise added to loading holes, 10 repetitions were set for each sample, the test samples were serum samples, due to the metabolism of mycophenolic acid, it failed to obtain natural high-value samples, and the high-value samples were only obtained by adding pure mycophenolic acid to clinical serum samples. Specific data was shown in table 1.

TABLE 1

Test results of sample repeatability

| Sample No | Measurement 1 | Measurement 2 | Measurement 3 | Measurement 4 | Measurement 5 | Measurement 6 |
|---|---|---|---|---|---|---|
| 1 | 1.35 | 1.42 | 1.27 | 1.28 | 1.21 | 1.41 |
| 2 | 1.47 | 1.32 | 1.23 | 1.45 | 1.21 | 1.58 |
| 3 | 2.23 | 2.57 | 2.12 | 2.63 | 2.53 | 2.47 |
| 4 | 3.23 | 3.45 | 3.67 | 3.21 | 3.55 | 3.63 |
| 5 | 4.11 | 4.26 | 4.38 | 4.57 | 4.81 | 4.21 |
| 6 | 5.05 | 5.21 | 5.03 | 5.47 | 5.28 | 5.33 |
| 7 | 7.23 | 7.53 | 7.28 | 7.4 | 7.21 | 7.22 |
| 8 | 9.67 | 9.48 | 10.02 | 9.58 | 9.77 | 9.12 |
| 9 | 15.33 | 13.77 | 14.32 | 15.03 | 14.68 | 13.97 |
| 10 | 18.21 | 19.22 | 19.98 | 17.23 | 19.32 | 18.25 |

| Sample No | Measurement 7 | Measurement 8 | Measurement 9 | Measurement 10 | Mean value | Standard deviation | CV |
|---|---|---|---|---|---|---|---|
| 1 | 1.35 | 1.36 | 1.56 | 1.25 | 1.346 | 0.101893 | 7.57% |
| 2 | 1.23 | 1.33 | 1.42 | 1.33 | 1.357 | 0.121019 | 8.92% |
| 3 | 2.65 | 2.78 | 2.55 | 2.43 | 2.496 | 0.196932 | 7.89% |
| 4 | 3.72 | 3.81 | 3.65 | 3.24 | 3.516 | 0.221068 | 6.29% |
| 5 | 4.35 | 4.27 | 4.71 | 4.32 | 4.399 | 0.225854 | 5.13% |
| 6 | 5.64 | 5.28 | 5.31 | 5.42 | 5.302 | 0.183836 | 3.47% |
| 7 | 7.83 | 7.08 | 7.73 | 7.09 | 7.36 | 0.259272 | 3.52% |
| 8 | 10.35 | 10.67 | 10.58 | 9.99 | 9.923 | 0.497997 | 5.02% |
| 9 | 14.25 | 15.97 | 14.31 | 15.08 | 14.671 | 0.679206 | 4.63% |
| 10 | 19.32 | 19.25 | 18.36 | 18.71 | 18.785 | 0.790713 | 4.21% |

EMBODIMENT 2

Preparation of a test strip:

1) 100 mL of 0.01% HAuCl4 aqueous solution was taken, boiled and rapidly added to 0.75 mL of 1% trisodium citrate aqueous solution, and then continuously boiled for about 5 min till orange red appeared, 50 nm colloidal gold particles were prepared at this time.

2) Colloidal gold solution and 200 μg/mL of mycophenolic acid monoclonal antibodies were mixed well and coupled for 3 h, then centrifuged to remove the supernatant, 1% BSA was added for sealing for 1 h.

3) The prepared marked conjugate was centrifuged and resupdended by a resuspending buffer solution (20 mm boric acid buffer solution, 0.5 g/L polyethylene glycol, 0.2 g/L alum, 4 g/L mannitol and 0.9% sodium chloride), a gold pad was soaked by a pretreating buffer solution (its components and content are consistent with the resuspending buffer solution) and dried for 2 h; a gold dispenser system was used to spray the resuspended solution on the gold pad, and then it was dried by an air dry oven for 6 h at 45° C.;

4) Line T on the nitrocellulose membrane represented mycophenolic acid-coupled BSA and the concentration was 1 mg/ml; line C represented goat-anti-mouse IgG and the concentration was 1 mg/ml; the mycophenolic acid-coupled BSA and goat-anti-mouse IgG are respectively dispersed on line T and line C of the nitrocellulose membrane, and then it was dried by an air dry oven for 6 h at 45° C.;

5) The sample pad (treated the same as embodiment 1), dried glassfiber membrane, blood filtering membrane, dried nitrocellulose membrane and absorbent paper were successively pasted on the bottom plate; a big reagent board was trimmed and loaded into a reagent card, was added a drying agent and sealed by an aluminium foil bag to obtain the test strip;

Preparation of a calibration curve was the same as embodiment 1.

Test of anti-interference capacity

Conventional blood was added to test samples for testing (50 mg/mL hemoglobin, 10 mmol/L triglyceride) the values obtained before and after adding interfering substances, and moreover, conventional clinical interfering substances were observed whether influencing the measured results.

TABLE 2

Test results of anti-interference capacity

| Sample No. | Before adding interfering substances | | | | After adding interfering substances | | | | Relative deviation |
|---|---|---|---|---|---|---|---|---|---|
| | Measurement 1 | Measurement 2 | Measurement 3 | Mean value | Measurement 1 | Measurement 2 | Measurement 3 | Mean value | |
| 1 | 1.45 | 1.32 | 1.36 | 1.376667 | 1.38 | 1.46 | 1.41 | 1.416667 | 2.91% |
| 2 | 1.67 | 1.73 | 1.82 | 1.74 | 1.65 | 1.72 | 1.88 | 1.75 | 0.57% |
| 3 | 1.37 | 1.54 | 1.42 | 1.443333 | 1.36 | 1.51 | 1.42 | 1.43 | −0.92% |
| 4 | 1.89 | 1.82 | 1.67 | 1.793333 | 1.76 | 1.62 | 1.81 | 1.73 | −3.53% |

It can be seen from table 2 that the relative deviation before and after adding interfering substances is less than 5% within the acceptable range.

EMBODIMENT 3

The test strip in embodiment 1 was applied to test whole blood samples and serum samples. Contrast of the test results between whole blood samples and serum samples:

The selected whole blood samples and serum samples were obtained from the same source, by contrasting the test results of the both two, the test reliability of the reagent to whole blood samples can be judged.

TABLE 3

Contrast of the test results between whole blood samples and serum samples:

| Sample No. | Measured value of serum | | | | Measured value of whole blood | | | | Relative deviation |
|---|---|---|---|---|---|---|---|---|---|
| | Measurement 1 | Measurement 2 | Measurement 3 | Mean value | Measurement 1 | Measurement 2 | Measurement 3 | Mean value | |
| 1 | 1.45 | 1.32 | 1.36 | 1.376666667 | 1.36 | 1.35 | 1.51 | 1.406667 | 2.18% |
| 2 | 1.67 | 1.73 | 1.82 | 1.74 | 1.65 | 1.83 | 1.72 | 1.733333 | −0.38% |
| 3 | 1.37 | 1.54 | 1.42 | 1.443333333 | 1.41 | 1.43 | 1.5 | 1.446667 | 0.23% |
| 4 | 1.89 | 1.82 | 1.67 | 1.793333333 | 1.84 | 1.76 | 1.72 | 1.773333 | −1.12% |
| 5 | 0.58 | 0.61 | 0.68 | 0.623333333 | 0.58 | 0.67 | 0.65 | 0.633333 | 1.60% |
| 6 | 0.74 | 0.65 | 0.72 | 0.703333333 | 0.68 | 0.78 | 0.72 | 0.726667 | 3.32% |
| 7 | 1.05 | 1.03 | 1.02 | 1.033333333 | 1.05 | 0.99 | 1.03 | 1.023333 | −0.97% |
| 8 | 1.13 | 1.24 | 1.15 | 1.173333333 | 1.07 | 1.24 | 1.32 | 1.21 | 3.13% |
| 9 | 2.32 | 2.24 | 2.36 | 2.306666667 | 2.31 | 2.27 | 2.41 | 2.33 | 1.01% |
| 10 | 1.32 | 1.41 | 1.37 | 1.366666667 | 1.35 | 1.32 | 1.34 | 1.336667 | −2.20% |

It can be seen from the above table that the deviation between whole blood samples and serum samples is within 5%, which is acceptable.

Contrast of stability:

The shelf life of the test strip prepared in the present invention is 18 months at 2-30° C., and the shelf life of the contrast reagent, namely, the mycophenolic acid kit (enzyme multiplied immunoassay technique) produced by Siemens Medical Diagnosis Products (Shanghai) Co., Ltd. is 18 months at 2-8° C. In the aspect of storage temperature, the test strip of the present invention is superior to the contrast reagent.

Contrast of linear range: the linear range of this experiment reagent is 0-20 μg/ml, the linear range of the contrast reagent, namely, the mycophenolic acid kit (enzyme multiplied immunoassay technique) produced by Siemens Medical Diagnosis Products (Shanghai) Co., Ltd. is 0-15 μg/ml, and THE linear range of the contrast reagent, namely, the mycophenolic acid homogeneous enzyme immunoassay reagent produced by EVERMED is 0-16 μg/ml. In the aspect of linear range, the test strip of the present invention is wider than the contrast reagent.

In the aspect of clinic correlation: test samples of the test strip provided by the present invention include serum, plasma and whole blood, while the test samples of the contrast reagent exclude whole blood. Due to the existence of hemocyte in whole blood, whole blood cannot be loaded on the machine. The contrast reagent is the mycophenolic acid kit (enzyme multiplied immunoassay technique) produced by Siemens Medical Diagnosis Products Co., Ltd. Contrast results of the clinic correlation are shown in table 4 and FIG. 1, and it can be seen that the clinic correlation is more than 0.9, conforming to clinical needs.

TABLE 4

Contrast results of the clinic correlation (unit: μg/mL)

| Sample No. | Test strip in embodiment 1 | Contrast reagent |
|---|---|---|
| 1 | 0.31 | 0.41 |
| 2 | 11.35 | 11.12 |
| 3 | 5.31 | 5.28 |
| 4 | 3.42 | 3.27 |
| 5 | 2.54 | 2.36 |
| 6 | 4.35 | 4.21 |
| 7 | 0.72 | 0.75 |

TABLE 4-continued

Contrast results of the clinic correlation (unit: μg/mL)

| Sample No. | Test strip in embodiment 1 | Contrast reagent |
|---|---|---|
| 8 | 1.24 | 1.31 |
| 9 | 1.33 | 1.28 |
| 10 | 2.53 | 2.36 |
| 11 | 2.42 | 2.31 |
| 12 | 5.36 | 5.28 |
| 13 | 10.25 | 10.11 |
| 14 | 7.35 | 7.21 |
| 15 | 15.24 | 15.11 |
| 16 | 16.25 | 13 |
| 17 | 7.25 | 6.83 |
| 18 | 1.56 | 1.32 |
| 19 | 1.47 | 1.58 |
| 20 | 12.11 | 11.67 |
| 21 | 1.45 | 1.33 |
| 22 | 3.24 | 3.54 |
| 23 | 6.31 | 6.52 |
| 24 | 10.26 | 9.47 |
| 25 | 2.57 | 2.61 |
| 26 | 3.1 | 2.91 |
| 27 | 3.11 | 3.01 |
| 28 | 14.32 | 13.99 |
| 29 | 8.67 | 8.21 |
| 30 | 9.22 | 9.01 |

It can be seen from the above embodiments that the test strip provided by the present invention can rapidly test the content of mycophenolic acid in blood samples, and the testing instrument has low cost, simple and rapid operation; the test strip has good stability and can be stored at room temperature for transportation with 18 months of shelf life at 2-30° C.; meanwhile test samples are extensive, including serum samples, plasma samples and whole blood samples.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A test strip for testing the content of mycophenolic acid, comprising a bottom plate and a sample pad, a glassfiber membrane, a nitrocellulose membrane and an absorbent paper which are successively lapped on a surface of the bottom plate, wherein
the sample pad is treated by a sample pad treatment fluid, and the sample pad treatment fluid comprises a buffer solution, an active protein and a surfactant, wherein the active protein is bovine serum albumin;
the glassfiber membrane is treated by a glassfiber membrane treatment fluid, and the glassfiber membrane is coated by a mycophenolic acid specific-antibody conjugate; and the mass concentration of the mycophenolic acid specific-antibody conjugate is 0.1-0.3%, and the coating concentration of the mycophenolic acid specific-antibody conjugate is 0.5-1 mg/mL, wherein the glassfiber membrane treatment fluid comprises a basal solution and following components at concentrations: 0.5-5 g/L polyethylene glycol 6000, 3-15 g/L mannitol, 0.1-1.5 g/L alum and 0.8%-1.0% sodium chloride; and the basal solution is a TRIS buffer solution; and
the nitrocellulose membrane is provided with a detection line and quality control line, a mycophenolic acid protein conjugate is sprayed on the detection line, the concentration of the mycophenolic acid protein conjugate is 1-3 mg/ml, and the spraying amount is 1-3 µL/cm.

2. The test strip according to claim 1, wherein the buffer solution in the sample pad treatment fluid is selected from one or more of PBS buffer solution, TRIS buffer solution and glycine buffer solution; the surfactant in the sample pad treatment fluid is selected from one or more of polyoxyethylenesorbitan monolaurate and polyoxyethylenesorbitan monooleate.

3. The test strip according to claim 1, wherein the conjugate in the mycophenolic acid specific-antibody conjugate is a colloidal gold particle or a fluorescent microsphere.

4. A preparation method of the test strip according to claim 1, comprising the following steps of:
1) treating the sample pad by the sample pad treatment fluid to obtain a treated sample pad;
2) mixing mycophenolic acid monoclonal antibodies and the conjugate for coupling and sealing to obtain a mycophenolic acid specific-antibody conjugate; spraying the mycophenolic acid specific-antibody conjugate on the treated glassfiber membrane to obtain the glassfiber membrane coated by the mycophenolic acid specific-antibody conjugate;
3) Spraying the mycophenolic acid protein conjugate on the detection line of the nitrocellulose membrane and spraying goat-anti-mouse IgG on the quality control line to obtain a nitrocellulose membrane sprayed with the detection line and quality control line;
4) successively lapping and pasting the treated sample pad, the glassfiber membrane coated by the mycophenolic acid specific-antibody conjugate, the nitrocellulose membrane provided with the detection line and quality control line as well as the absorbent paper on the surface of the bottom plate to obtain the test strip;
wherein, there is no limitation on an execution sequence of steps 1), 2) and 3).

5. The preparation method according to claim 4, wherein the concentration of mycophenolic acid monoclonal antibodies of the coupling system in step 2) is 100-500 µg/mL; and the coupling time is 2.5-3.5h.

6. The preparation method according to claim 4, wherein the mycophenolic acid protein conjugate is sprayed after mixed with a spraying buffer solution;
components of the spraying buffer solution are the same as those of the glassfiber membrane treatment fluid.

7. A preparation method of the test strip according to claim 2, comprising the following steps of:
1) treating the sample pad by the sample pad treatment fluid to obtain a treated sample pad;
2) mixing mycophenolic acid monoclonal antibodies and the conjugate for coupling and sealing to obtain a mycophenolic acid specific-antibody conjugate; spraying the mycophenolic acid specific-antibody conjugate on the treated glassfiber membrane to obtain the glassfiber membrane coated by the mycophenolic acid specific-antibody conjugate;
3) Spraying the mycophenolic acid protein conjugate on the detection line of the nitrocellulose membrane and spraying goat-anti-mouse IgG on the quality control line to obtain a nitrocellulose membrane sprayed with the detection line and quality control line;
4) successively lapping and pasting the treated sample pad, the glassfiber membrane coated by the mycophenolic acid specific-antibody conjugate, the nitrocellulose membrane provided with the detection line and quality control line as well as the absorbent paper on the surface of the bottom plate to obtain the test strip;
wherein, there is no limitation on an execution sequence of steps 1), 2) and 3).

8. The preparation method according to claim 7, wherein the concentration of mycophenolic acid monoclonal antibodies of the coupling system in step 2) is 100-500 µg/mL; and the coupling time is 2.5-3.5h.

9. The preparation method according to claim 7, wherein the mycophenolic acid protein conjugate is sprayed after mixed with a spraying buffer solution; components of the spraying buffer solution are the same as those of the glassfiber membrane treatment fluid.

10. A preparation method of the test strip according to claim 3, comprising the following steps of:
1) treating the sample pad by the sample pad treatment fluid to obtain a treated sample pad;
2) mixing mycophenolic acid monoclonal antibodies and the conjugate for coupling and sealing to obtain a mycophenolic acid specific-antibody conjugate; spraying the mycophenolic acid specific-antibody conjugate on the treated glassfiber membrane to obtain the glassfiber membrane coated by the mycophenolic acid specific-antibody conjugate;
3) Spraying the mycophenolic acid protein conjugate on the detection line of the nitrocellulose membrane and spraying goat-anti-mouse IgG on the quality control line to obtain a nitrocellulose membrane sprayed with the detection line and quality control line;
4) successively lapping and pasting the treated sample pad, the glassfiber membrane coated by the mycophenolic acid specific-antibody conjugate, the nitrocellulose membrane provided with the detection line and quality control line as well as the absorbent paper on the surface of the bottom plate to obtain the test strip;
wherein, there is no limitation on an execution sequence of steps 1), 2) and 3).

11. The preparation method according to claim 10, wherein the concentration of mycophenolic acid monoclonal antibodies of the coupling system in step 2) is 100-500 μg/mL; and the coupling time is 2.5-3.5h.

12. The preparation method according to claim 10, wherein the mycophenolic acid protein conjugate is sprayed after mixed with a spraying buffer solution; components of the spraying buffer solution are the same as those of the glassfiber membrane treatment fluid.

13. A kit comprising the test strip according to claim 1, wherein the kit further comprises a mycophenolic acid quality control (QC) substance.

14. The kit according to claim 13, wherein the mycophenolic acid QC substance is obtained by mixing and lyophilizing pure mycophenolic acid and a lyophilized buffer solution.

15. The kit according to claim 14, wherein the lyophilized buffer solution comprises a basal solution and the following components "at concentrations": 2-6 g/L polyethylene glycol, 3-8 g/L trehalose, 5-20 g/L mannitol, 1 wt % polyvinylpyrrolidone; the basal solution is selected from one or more of TRIS buffer solution, phosphoric acid buffer solution, boric acid buffer solution and phosphate buffer solution; pH of the basal solution is 7.6-8.6; the solute concentration of the basal solution is 50-200 mmol/L.

16. A kit comprising the test strip according to claim 2, wherein the kit further comprises a mycophenolic acid QC substance.

\* \* \* \* \*